US011446455B2

(12) United States Patent
Davoine (10) Patent No.: US 11,446,455 B2
(45) Date of Patent: Sep. 20, 2022

(54) MEDICAL VENTILATOR WITH INTERNAL CASING INCLUDING A MOTORIZED MICRO-BLOWER AND GAS CIRCUITS

(71) Applicant: Air Liquide Medical Systems, Antony (FR)

(72) Inventor: Romain Davoine, Grenoble (FR)

(73) Assignee: Air Liquide Medical Systems, Antony (FR)

(*) Notice: Subject to any disclaimer, the term of this patent is extended or adjusted under 35 U.S.C. 154(b) by 261 days.

(21) Appl. No.: 16/916,932

(22) Filed: Jun. 30, 2020

(65) Prior Publication Data

US 2021/0001068 A1 Jan. 7, 2021

(30) Foreign Application Priority Data

Jul. 5, 2019 (FR) ...................................... 1907508

(51) Int. Cl.
*A61M 16/00* (2006.01)
*A61M 16/06* (2006.01)

(52) U.S. Cl.
CPC ......... *A61M 16/0063* (2014.02); *A61M 16/06* (2013.01); *A61M 16/0672* (2014.02); *A61M 2016/003* (2013.01); *A61M 2016/0027* (2013.01); *A61M 2202/0208* (2013.01); *A61M 2205/75* (2013.01); *A61M 2205/8206* (2013.01)

(58) Field of Classification Search
CPC .... F04D 29/424; F04D 17/162; F04D 25/082; F04D 29/5806; F04D 27/009; A61M 16/125; A61M 16/0063; A61M 16/0066; A61M 16/105; A61M 2205/75; A61M 2205/7545; A61M 16/1055; A61M 16/0672; A61M 2205/8206; A61M 2205/3606; A61M 2202/0208; A61M 16/06; A61M 2016/003; A61M 16/024; A61M 2205/362; A61M 2016/0027; H02K 11/20; H02K 7/14; H02K 9/227
See application file for complete search history.

(56) References Cited

U.S. PATENT DOCUMENTS

| 6,557,554 B1* | 5/2003 | Sugiura | A61M 16/0096 128/204.21 |
| 7,753,996 B1* | 7/2010 | Deane | A61M 16/101 128/205.24 |
| 8,440,004 B2* | 5/2013 | Taylor | A61M 16/101 96/121 |

(Continued)

FOREIGN PATENT DOCUMENTS

| AU | 2018204819 B2 * | 2/2020 | ........ A61M 16/0003 |
| DE | 10 2014 009895 | 1/2015 | |

(Continued)

OTHER PUBLICATIONS

French Search Report for corresponding FR 1907508, dated Mar. 17, 2020.

*Primary Examiner* — Vinh T Lam
(74) *Attorney, Agent, or Firm* — Allen E. White (57) ABSTRACT

The invention relates to a respiratory assistance apparatus (10) comprising a rigid internal casing (1) comprising a motor compartment (3) within which a motorized micro-blower (2) is arranged. The casing (1) is formed from a first and a second half-casing (1a, 1b) which are rigidly connected to each other in a leaktight manner.

10 Claims, 5 Drawing Sheets

(56) References Cited

U.S. PATENT DOCUMENTS

| | | | |
|---|---|---|---|
| 8,517,012 B2* | 8/2013 | Daly | A61M 16/0069 |
| | | | 415/98 |
| 8,800,560 B2* | 8/2014 | Alfieri | A61M 16/0069 |
| | | | 55/482 |
| 9,427,538 B2* | 8/2016 | Daly | F04D 29/281 |
| 9,616,188 B2* | 4/2017 | Grasmuck | F04D 29/584 |
| 10,315,002 B2* | 6/2019 | DeVries | A61M 16/0883 |
| 10,463,827 B2* | 11/2019 | Feldhahn | A61M 16/0858 |
| 11,191,913 B2* | 12/2021 | Kenyon | F04D 29/4226 |
| 11,247,015 B2* | 2/2022 | DeVries | A61M 16/0808 |
| 11,278,700 B2* | 3/2022 | Van Schalkwyk | |
| | | | A61M 16/0066 |
| 2007/0193580 A1* | 8/2007 | Feldhahn | A61M 16/00 |
| | | | 128/204.18 |
| 2008/0257347 A1 | 10/2008 | Grasmuck | |
| 2008/0304986 A1 | 12/2008 | Kenyon et al. | |
| 2009/0084381 A1* | 4/2009 | DeVries | A61M 16/12 |
| | | | 128/204.21 |
| 2009/0291004 A1 | 11/2009 | Grasmuck | |
| 2012/0037160 A1* | 2/2012 | Sung | A61M 16/0066 |
| | | | 128/205.12 |
| 2012/0160245 A1* | 6/2012 | Leuschner | A62B 18/10 |
| | | | 128/204.26 |
| 2014/0345609 A1* | 11/2014 | Whitcher | C01B 13/0259 |
| | | | 128/202.26 |
| 2017/0203063 A1 | 7/2017 | Pecherer | |
| 2020/0368470 A1* | 11/2020 | Boulanger | A61M 16/0084 |

FOREIGN PATENT DOCUMENTS

| | | | | |
|---|---|---|---|---|
| EP | 2 165 078 | | 10/2010 | |
| EP | 2 102 504 | | 2/2017 | |
| EP | 2833953 B1 | * | 1/2019 | A61M 16/0003 |
| FR | 2 843 305 | | 2/2004 | |
| FR | 2 910 079 | | 6/2008 | |
| FR | 3 019 991 | | 10/2015 | |
| GB | 2567065 B | * | 6/2019 | A61M 16/0003 |
| WO | WO 2012 139681 | | 10/2012 | |
| WO | WO 2013 020167 | | 2/2013 | |
| WO | WO-2013020167 A1 | * | 2/2013 | A61M 16/0066 |
| WO | WO 2013 048238 | | 4/2013 | |
| WO | WO-2020161019 A1 | * | 8/2020 | A61M 16/0066 |

* cited by examiner

MEDICAL VENTILATOR WITH INTERNAL CASING INCLUDING A MOTORIZED MICRO-BLOWER AND GAS CIRCUITS

CROSS REFERENCE TO RELATED APPLICATIONS

This application claims the benefit of priority under 35 U.S.C. § 119 (a) and (b) to French Patent Application No. 1907508, filed Jul. 5, 2019, the entire contents of which are incorporated herein by reference.

BACKGROUND

The invention relates to a respiratory assistance apparatus, that is to say a medical ventilator for delivering a flow of oxygen-enriched air in order to treat one or more respiratory diseases in humans, which is equipped with a multi-functional casing containing a motorized micro-blower, for delivering a respiratory gas such as air or oxygen-enriched air, and gas circuits.

In order to assist certain patients with their respiratory function, use is made of respiratory assistance apparatuses, also called medical ventilators, delivering a respiratory gas, such as air or oxygen-enriched air, at a non-zero flow rate and/or at a pressure higher than atmospheric pressure (>1 atm).

These respiratory assistance apparatuses use a motorized micro-blower, also called a compressor or turbine, for aspirating ambient air and delivering it at a given pressure to the patients. The aspiration of the air by the micro-blower, during the functioning of its motor, is effected by virtue of one or more bladed wheels which are arranged on a rotary shaft driven in rotation by an electric motor, the one or more bladed wheels being movable in rotation in the internal compartment of a volute.

The air can be oxygen-enriched air, that is to say it can have additional oxygen added to it, especially when the patient is intended to receive, in the context of his or her treatment, a proportion of oxygen greater than 21% by volume.

Documents EP-A-2165078, EP-A-2102504, WO-A-2012/139681, US-A-2008/304986 and WO-A-2013/020167 describe micro-blowers of this type and respiratory assistance apparatuses equipped with such micro-blowers.

However, this type of respiratory assistance apparatus is often bulky, since it includes complex, e.g. meandering, internal gas circuits so as to ensure good cooling of the micro-blower and also to meet the ventilation requirements, especially to limit the losses of head and to ensure good ventilation performance and patient safety.

In view of the above, the problem addressed is therefore to be able to limit the overall size of a medical ventilator, especially of the type used for emergencies, while at the same time ensuring efficient cooling of the micro-blower and pneumatic compatibility and also meeting the ventilation requirements, i.e. loss of head, performance, patient safety.

The solution according to the invention is a respiratory assistance apparatus, that is to say a medical ventilator, comprising a rigid internal casing comprising a motor compartment within which a motorized micro-blower is arranged, characterized in that the casing is formed of a first and a second half-casing which are rigidly connected to each other in a leaktight manner, said rigid casing comprising:
an air inlet compartment comprising an air inlet opening in communication with the atmosphere, said air inlet compartment additionally being in fluidic communication with the motor compartment via at least one air outlet opening, i.e. one or more orifices for passage of gas,
a gas outlet compartment comprising a gas supply opening, said gas outlet compartment being fed with gas by the motorized micro-blower, typically with air or with oxygen-enriched air,
an oxygen circuit comprising an oxygen inlet and at least one oxygen outlet, said at least one oxygen outlet being in fluidic communication with the motor compartment, and
a venting circuit comprising an air inlet, formed in the air inlet compartment, and an air outlet.

Depending on the case, the respiratory assistance apparatus according to the invention may comprise one or more of the following technical features:
the first half-casing comprises:
at least part of the air inlet compartment,
at least part of the motor compartment,
at least part of the gas outlet compartment, and
the oxygen circuit comprising the oxygen inlet and said at least one oxygen outlet.
the second half-casing comprises:
at least part of the air inlet compartment, and
the venting circuit comprising the air inlet and the air outlet.
the venting circuit comprising an air outlet arranged parallel to the gas supply opening of the gas outlet compartment.
it comprises filtration means arranged upstream and/or downstream from the air inlet compartment, for example one or more filters of the HEPA type or similar (High Efficiency Particulate Air Filter), for filtering the ambient air and freeing the latter of any pollutants it may contain, such as dust, microorganisms, spores, etc.
the oxygen circuit comprises an oxygen inlet arranged parallel to the air outlet of the venting circuit.
the motor compartment comprises a peripheral wall surrounding at least part of the outer housing of the micro-blower, thus defining, with said outer housing, a space for passage of gas.
the oxygen circuit comprises at least one oxygen outlet opening into the gas passage space situated between the peripheral wall of the motor compartment and the outer housing of the micro-blower, so as to feed said space of the motor compartment with oxygen and to mix said oxygen there with air coming from the air inlet compartment.
the motorized micro-blower additionally comprises a volute defining a wheel compartment which accommodates a bladed wheel supported by a motor shaft driven by the motor contained in the housing of the motorized micro-blower.
the volute lies over the housing of the motor.
the motor shaft projects into the wheel compartment.
the electric motor drives the rotation of the motor shaft supporting the bladed wheel.
the volute comprises a volute opening in fluidic communication with, on the one hand, the gas passage space and, on the other hand, the wheel compartment, in such a way as to feed the wheel compartment with gas coming from the gas passage space, said gas being sucked into said wheel compartment by the rotations of the bladed wheel when the latter is set in rotation by the motor and the shaft that supports it.

the volute additionally comprises an outlet opening in fluidic communication with, one the one hand, the wheel compartment and, on the other hand, the gas outlet compartment, in such a way as to feed said gas outlet compartment with gas coming from the wheel compartment, that is to say gas emerging from the wheel compartment on account of the rotations of the bladed wheel. In other words, the gas is expelled from the wheel compartment by the rotations of the bladed wheel when the latter is set in rotation by the motor and the shaft that supports it.

the gas entering and/or leaving the wheel compartment of the volute is air or oxygen-enriched air.

the micro-blower is equipped with an electric motor.

the (expanded) oxygen which is introduced into the motor compartment, and which mixes with the air located there, is generally at a "cold" temperature, that is to say below the ambient temperature, typically 3 to 5° C. below, depending on the flow rate delivered, and its contact with the housing of the micro-blower in the gas passage space will permit absorption of some of the calories generated by the motor during its operation (acceleration and braking in ventilation), and the air/oxygen mixture will then reheat before being sent to the volute.

the peripheral wall of the motor compartment forms a sleeve around at least part of the outer housing of the micro-blower.

at least some of the air/oxygen gas mixture circulates in the gas passage space, sweeping across the outer wall of the housing of the micro-blower.

the motor compartment additionally comprises at least one opening in fluidic communication with the motor compartment, in particular with the gas passage space, in order to extract at least some of the gas, typically air or a gaseous mixture of air and oxygen, present in the motor compartment, in particular in the gas passage space.

the rigid casing forms a shell.

it additionally comprises control means configured to control the functioning or shut-down of the electric motor, that is to say the rotations and the discontinuation of rotation (i.e. braking or deceleration) of the wheel of the micro-blower.

the control means comprise at least one microprocessor, preferably at least one microcontroller, and components for powering the motor, such as transistors or the like.

the control means comprise at least one electronic board comprising said at least one microprocessor and components for powering the motor.

the microprocessor uses one or more algorithms.

the control means are supplied with electric current.

it comprises a HMI.

it comprises a viewing screen, i.e. for displays, information.

the blades of the bladed wheel form walls or structures spaced apart from one another and arranged radially on the first face of the bladed wheel.

the bladed wheel comprises 10 to 30 blades, also called "vanes".

the bladed wheel has a diameter of between 20 and 80 mm, preferably of between 30 and 60 mm.

the bladed wheel is driven by the motor at a speed of up to 70,000 rpm, typically 30,000 or 40,000 rpm.

the blades form walls that are curved, that is to say non-rectilinear.

the bladed wheel is made of a polymer material, preferably transformed by thermoplastic injection.

the blades are formed in one piece with the first face of the bladed wheel.

the electric motor comprises an outer housing forming a rigid structure surrounding the rotor and the stator of the motor.

the electric motor comprises electric cables or wires for connecting it electrically to a source of electric current, such as the mains supply, or one or more electric batteries, especially rechargeable ones.

the second face of the bladed wheel, which faces the housing of the motor, has no blades and is plane.

the electric motor is of the brushless type.

the bladed wheel is arranged movably in rotation within the wheel compartment of the volute.

the volute comprises an upper semi-volute and a lower semi-volute which are fixed to each other, preferably in a leaktight manner, for example by bonding and/or with interpositioning of a seal.

the motor shaft supporting the bladed wheel extends through the lower semi-volute.

a gas supply opening of the gas outlet compartment is connected fluidically to a gas supply conduit, such as a flexible tube, feeding a respiratory interface, such as a breathing mask, nasal cannulas or the like, such that the respiratory gas leaving the micro-blower is distributed to a patient, typically air or oxygen-enriched air.

the oxygen circuit comprises an oxygen inlet supplied via an oxygen source, such as a pressurized oxygen canister or a wall socket for delivery of oxygen through oxygen supply channels, for example a hospital network.

The respiratory assistance apparatus of the invention is of the type delivering continuous pressure (CPAP) or of the type with two pressure levels (BiPAP), or an emergency respirator.

The apparatus is designed to deliver a flow of air or of oxygen-enriched air (including up to about 100% oxygen).

The invention also relates to an installation for supplying respiratory gas to a patient, comprising a respiratory assistance apparatus according to the invention, an oxygen source, such as a pressurized oxygen canister, connected fluidically to said respiratory assistance apparatus, a flexible conduit connected fluidically to said respiratory assistance apparatus and supplied with gas by the latter, and a respiratory interface, such as a mask, nasal cannulas or the like, supplied with gas by said flexible conduit, typically with air or a mixture of air and oxygen.

BRIEF DESCRIPTION OF THE DRAWINGS

The invention will now be better understood by virtue of the following detailed description, which is provided by way of a non-limiting illustration, and with reference to the appended figures, in which.

DETAILED DESCRIPTION OF PREFERRED EMBODIMENTS

FIG. 1 to FIG. 8 show an embodiment of a rigid casing 1 according to the present invention for a respiratory assistance apparatus or medical ventilator 10 comprising a motorized micro-blower 2, also called a turbine or compressor.

According to the invention, the rigid casing 1 is formed of two parts, namely a first and a second half-casing 1a, 1b, which are rigidly connected to each other in a leaktight manner, that is to say schematically in the manner of the two shells or valves of a bivalve.

Figure 1:
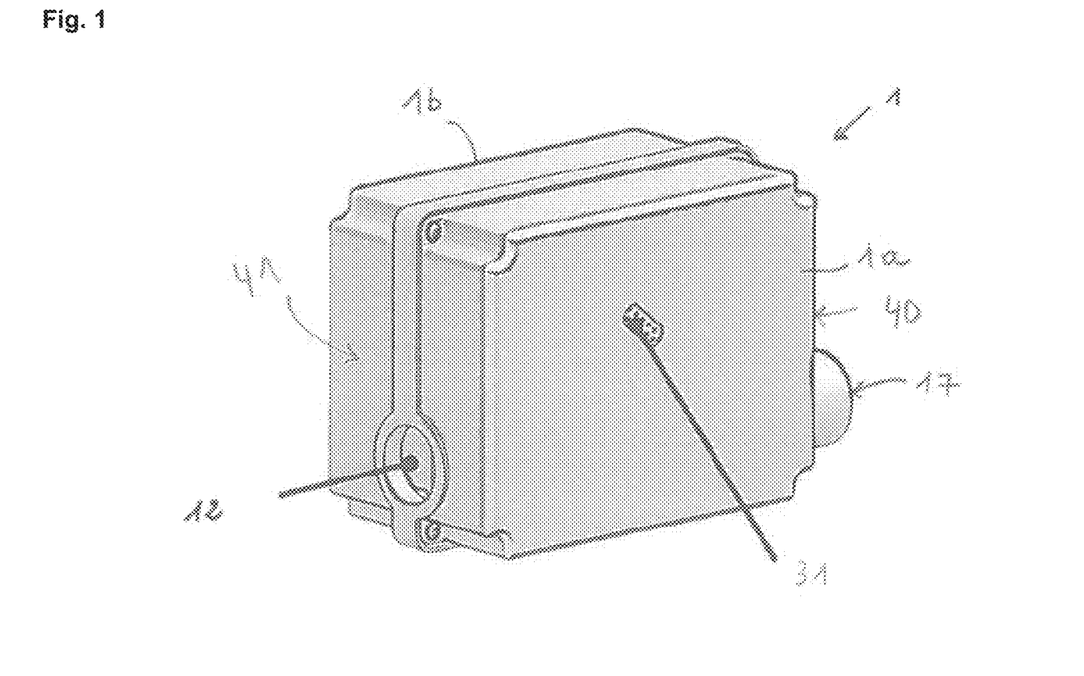
FIG. 1 shows a side view of a rigid casing for a respiratory assistance apparatus according to the invention.

In the embodiment shown, the casing 1 also has the general shape of a rectangular parallelepiped, as can be seen from FIG. 1. More generally, the rigid casing 1 comprises:
- a motor compartment 3 within which a motorized micro-blower 2 is arranged,
- an air inlet compartment 11 comprising an air inlet opening 12 in fluidic communication with the ambient atmosphere and also with the motor compartment 3 via an air outlet opening 13, such that the air entering through the air inlet opening 12 can feed the motor compartment 3,
- a gas outlet compartment 14 comprising a gas supply opening 15, which is fed with gas by the motorized micro-blower 2 via a gas evacuation conduit 29, as is explained below,
- an oxygen circuit or passage 16 comprising an oxygen inlet 17 and one or more oxygen outlets 18, preferably a plurality of orifices or oxygen outlets 18, in fluidic communication with the motor compartment, so as to feed the motor compartment 3 with oxygen and to there form a gaseous mixture between the air coming from the air inlet compartment 11 and the oxygen distributed via the one or more oxygen outlets 18, and
- a venting circuit or passage 19 comprising an air inlet 20, formed in the air inlet compartment 11, and an air outlet 21, which allows the patient to be able to breathe even in the event of a failure of the micro-blower 2 or the like.

The ambient air can be filtered, before and/or after it enters the air inlet compartment 11, in order to purify it, that is to say in order to free it of the pollutants, such as dust, spores, microorganisms or the like, that it may contain, in particular by filtration, for example with one or more HEPA filters.

The first half-casing 1a comprises at least part of the air inlet compartment 11, at least part of the motor compartment 3, at least part of the gas outlet compartment 14, and the oxygen circuit 16 with the oxygen inlet 17 and the one or more oxygen outlets 18.

Moreover, the second half-casing 1b comprises at least part of the air inlet compartment 11 and the venting circuit 19 with the air inlet 20 and the air outlet 21. The role of the venting circuit 19 is to allow a patient to breathe through this circuit in the event of failure of the micro-blower 2, so as to avoid an accident.

The venting circuit or passage 19 extends through the casing and comprises an air outlet 21, arranged parallel to the gas supply opening 15 of the gas outlet compartment 14. Similarly, the oxygen circuit 16 comprises an oxygen inlet 17 arranged parallel to the air outlet 21 of the venting circuit 19. In other words, as can be seen in FIG. 2, the air outlet 21, the gas supply opening 15 and the oxygen inlet 17 are arranged on the same face 40 of the casing, while the air inlet opening 12 is situated on an opposite face 41, as can be seen in FIG. 1.

Figure 2:
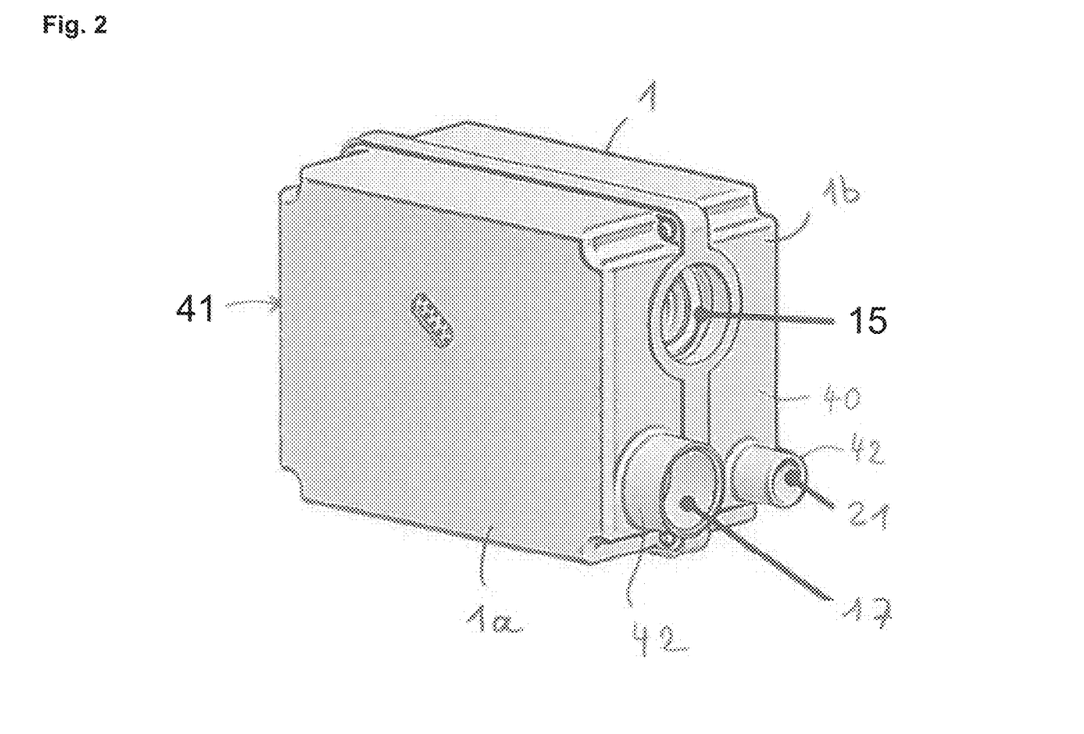
FIG. 2 is another side view of the casing from FIG. 1.
Figure 3:
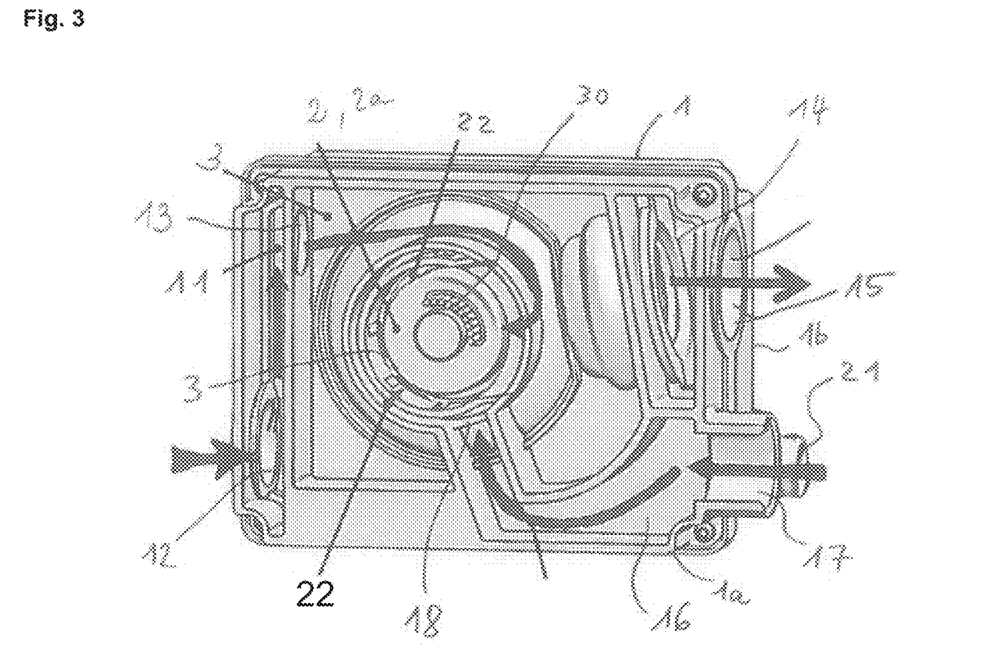
FIG. 3 is a sectional view of the casing from FIG. 1.
Figure 4:
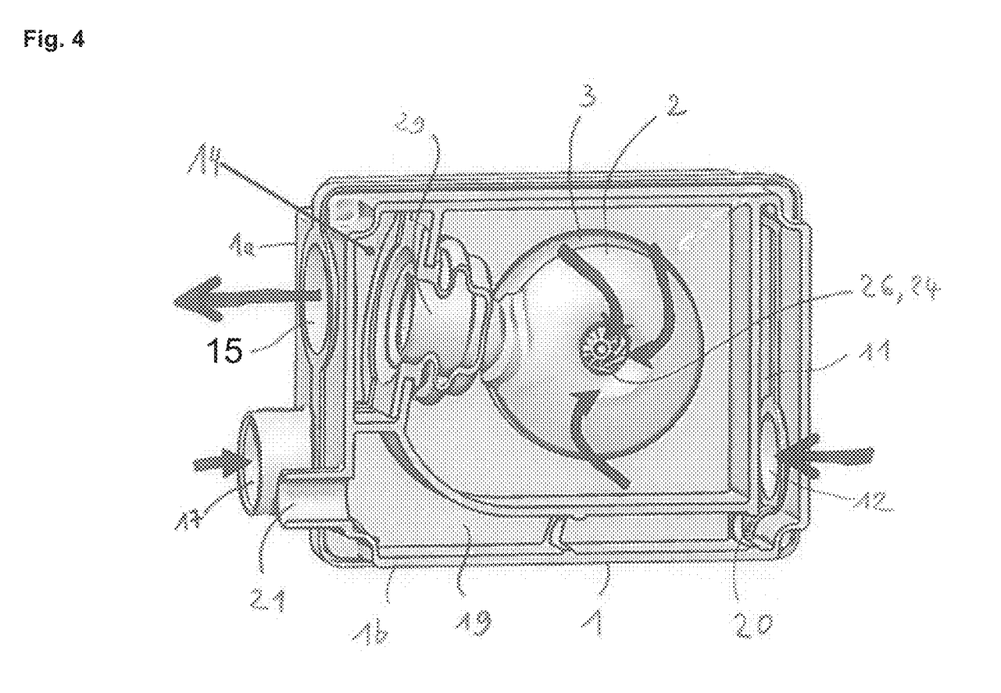
FIG. 4 is a sectional view of the casing from FIG. 1.

Preferably, the oxygen inlet 17 and the air outlet 21 are arranged on tubular, typically cylindrical, elements or connectors protruding from the surface of the face 40 of the casing 1, as is illustrated in FIG. 2.

The motorized micro-blower 2 is equipped with an electric motor (not visible), for example a brushless motor, arranged in an outer housing 2a comprising a rigid peripheral wall for protecting the motor, that is to say typically the stator and the rotor of the motor.

The rigid peripheral wall of the housing 2a can be formed from a metal alloy, for example an alloy of aluminium or Zamak (alloy of zinc, aluminium, magnesium and copper), or from a polymer or thermoplastic, for example PET or PA. The housing 2a generally has a circular cross section, that is to say a general cylindrical shape. It can also have cooling blades or structures serving as a radiator.

Preferably, the electric motor is brushless and/or is designed to reach a speed of rotation that is typically of the order of 30,000 to 40,000 rpm, or even up to 70,000 rpm or above.

The supply of electric current to the motor of the micro-blower 2, to permit the operation of the latter, is traditionally effected by means of a suitable connection system, for example by means of one or more connectors, sockets 31, electrical wires or cables 30 for connecting the casing 1, the apparatus and/or the micro-blower 2 to the electricity network for example, or to one or more electrical supply batteries.

During its operation, the motor of the micro-blower 1 drives the rotation of a rotary shaft 25, also called a motor shaft, supporting a bladed wheel 24, also called a "vane wheel'. This bladed wheel 24 preferably has a circular cross section of between 20 and 80 mm, typically of between 30 and 60 mm. The bladed wheel 24 comprises a first face supporting the blades, also called "vanes", and a second face without blades, that is to say plane, which is additionally situated opposite the housing 2a of the motor 2.

The bladed wheel 24 is arranged so as to be rotationally movable inside the internal wheel compartment 27 of a volute 23 surmounting the electric motor and the housing 2a, so as to generate a gaseous flow at a pressure that is above the atmospheric pressure (>1 atm).

Preferably, the bladed wheel 24 and the volute 23 are made of polymer material(s), for example a thermoplastic (e.g. PEEK, PA, etc.), or a metal alloy, for example an aluminium-based alloy.

The volute 23 can be formed by two semi-volutes, namely a lower semi-volute and an upper semi-volute, which are joined and fixed rigidly to each other in a leaktight manner, for example by bonding or other means. A seal can be interposed between these semi-volutes.

The volute 23 has a generally circular cross section. It additionally has a central gas opening or passage 26 through which the gas is sucked into the wheel compartment 27 situated in the volute 23, during the rotations of the wheel 24, and a gas flow outlet orifice 28, through which the gas flow generated in the wheel compartment 27, during the rotations of the wheel 4, exits the micro-blower 2.

The gas flow is then conveyed through an evacuation conduit 29, which is fluidically connected to the gas flow outlet orifice 28, as far as the gas outlet compartment 14 comprising a gas supply opening 15.

In other words, the gas outlet compartment 14 is fed with gas by the micro-blower 2 via the evacuation conduit 29, typically with air or a mixture of air and oxygen. The gas flow then leaves the gas outlet compartment 14 via the gas supply opening 15, before then being sent to the patient via a flexible tube feeding a respiratory interface, such as a mask, nasal cannulas or the like (not shown).

The volute 23 is in fluidic communication, directly or indirectly, with the motor compartment 3 within which in particular the mixing of air and oxygen is effected when the air flow has to be enriched with oxygen.

At least part of the outer housing 2a of the electric motor of the micro-blower 2 is arranged, that is to say projecting, in the motor compartment 3 of the casing 1 of the ventilation apparatus. More precisely, the motor compartment 3 is delimited by (at least) a peripheral wall 3a surrounding at least part of the outer housing 2a of the micro-blower 2, defining with the outer housing 2a a gas passage space 22 within which the gas flow can circulate, in particular an air/oxygen mixture, which will sweep across the wall of the housing 2a before being evacuated to the volute 23. In other words, the peripheral wall of the motor compartment 3 forms a sleeve around the housing 2a.

The motor compartment 3 additionally comprises, arranged in its peripheral wall 3a, one or more air inlet orifices 13 in fluidic communication with the gas passage space 22, in order to feed the motor compartment 3, including the space 22, with air.

Moreover, it additionally comprises at least one oxygen inlet orifice 16, preferably a plurality of oxygen inlet orifices 16, in fluidic communication with the motor compartment 12, including the gas passage space 22, in order to feed the motor compartment 12 and the space 22 with oxygen and to thereby obtain a gaseous flow of air and oxygen, called an air//oxygen mixture. Indeed, some of the gaseous flow is propelled by the flow rate of oxygen entering the casing.

In other words, the motor compartment 12, in particular the space 22, is fed with air from the one or more air inlet orifices 15 and with oxygen from the one or more oxygen inlet orifices 16, which leads to the air/oxygen mixture being obtained there. At least part of said air/oxygen mixture comes into contact with the housing 2a of the micro-blower 2, that is to say it sweeps across the outer surface (i.e. wall) of the housing 2a of the motor of the micro-blower 2, so as to capture some of the calories (i.e. the heat) generated by the motor during the operation of the latter.

The flow of the air/oxygen mixture circulating in the space 22 reheats there upon contact with the housing 2, then leaves the space 22, and therefore the motor compartment 12, via one or more gas outlet openings 17, bringing the gas passage space 22 and the motor compartment 12 into fluidic communication with the gaseous mixture compartment 18 surrounding the volute 5, in such a way as to extract at least some of the air/oxygen gas mixture which is present in the space 22 and which is reheated upon contact with the housing 2 of the motor, and then to feed the gas mixture compartment 18 with this air/oxygen gas mixture.

This air/oxygen gas mixture is then sucked into the wheel compartment 6 of the volute 5, via its central gas opening or passage 7, during the rotations of the wheel 4, that is to say during the operation of the electric motor of the micro-blower 1, which drives the wheel 4 in rotation, thus creating suction.

According to one embodiment, an intermediate chamber or compartment can be provided between the space 22 of the motor compartment 3 and the inlet 26 of the volute 23, serving to receive the air or the air/oxygen gas mixture, coming from the motor compartment 3, before it penetrates the volute 23, by being aspirated by the rotary wheel 24, during the rotations thereof.

The air/oxygen gas mixture then leaves the wheel compartment 6 of the micro-blower 1, via the gas flow outlet passage 8, before then being sent to a patient who inhales this gaseous mixture, for example via a flexible tube and a respiratory interface such as a breathing mask or the like.

Figure 5:
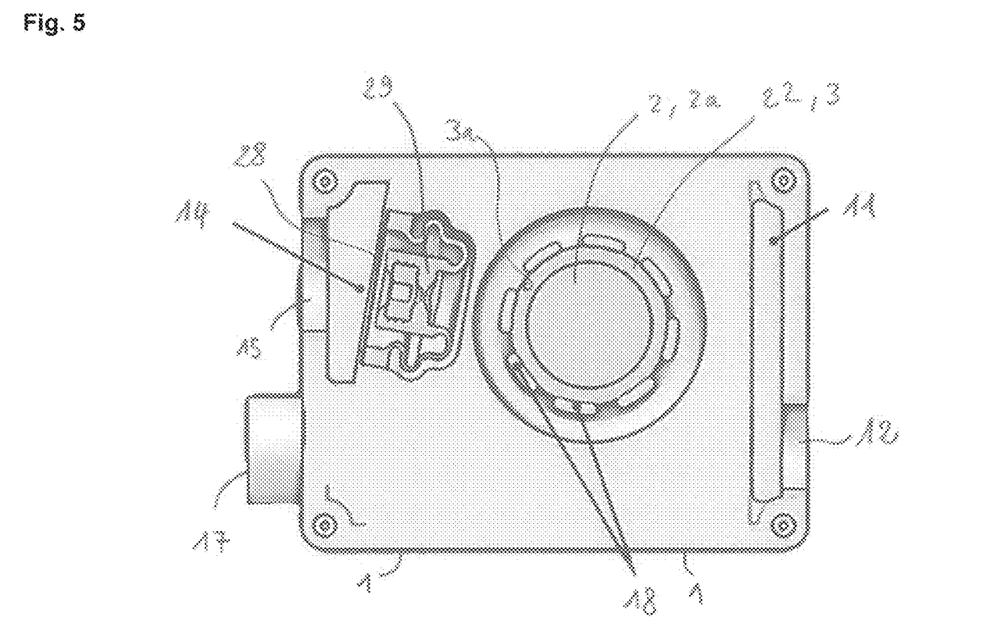
FIG. 5 is a sectional view of the casing from FIG. 1.
Figure 6:
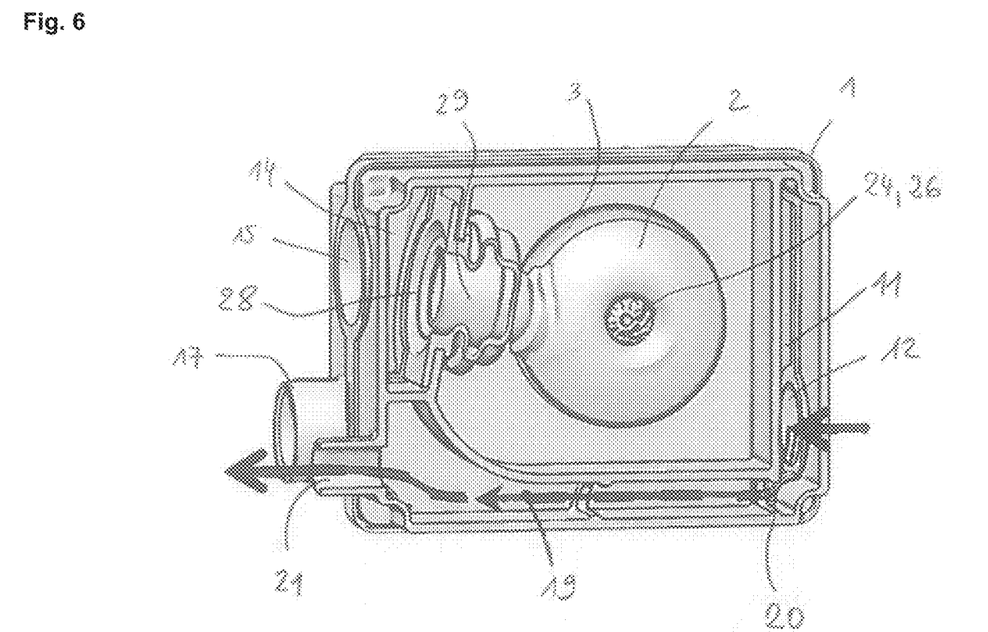
FIG. 6 is a sectional view of the casing from FIG. 1.
Figure 7:
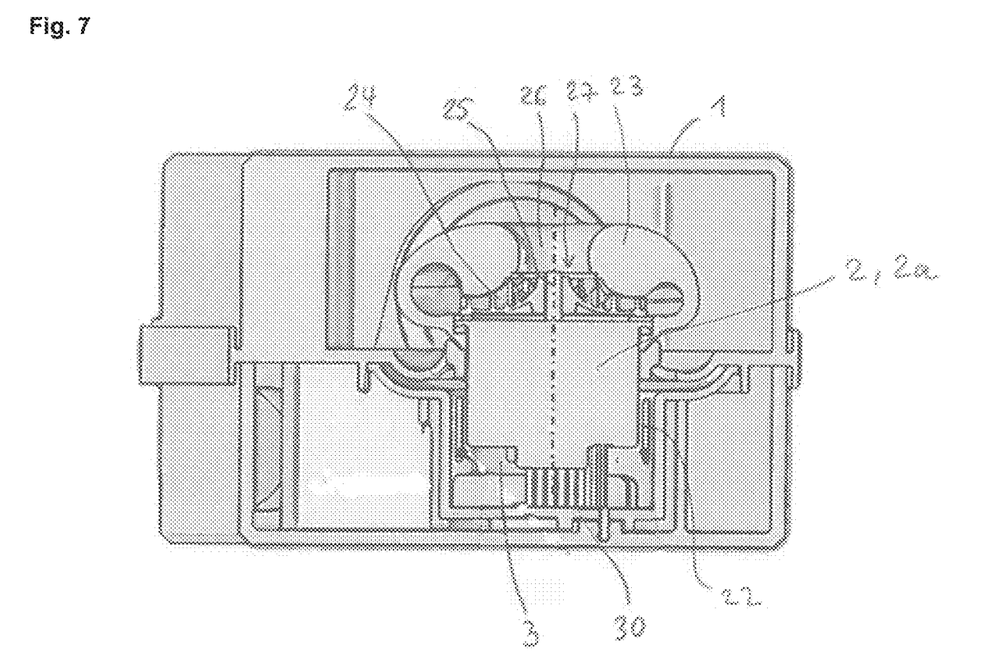
FIG. 7 is a sectional view of the casing from FIG. 1.
Figure 8:
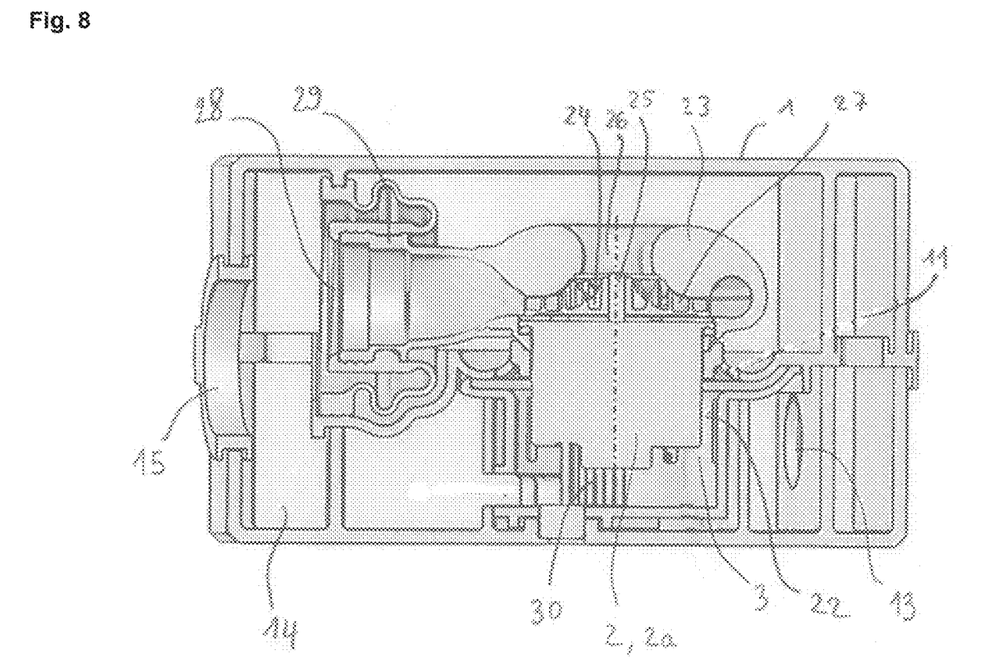
FIG. 8 is a sectional view of the casing from FIG. 1.

Preferably, the space 22 for the gas has an annular general shape, when the housing 2 and the motor compartment 12 each have a circular cross section, that is to say generally cylindrical three-dimensional shapes, as is illustrated in FIG. 5.

As has already been mentioned, the air/oxygen mixture is aspirated by the bladed wheel 4, during the rotations of the latter, and circulates in the space 22 and sweeps across, that is to say "washes", the outer surface 2a of the housing 2, in such a way as to cool it by capturing some of the calories generated by the motor, during the operation of the latter.

Traditionally, the apparatus 10 moreover comprises control means, such as an electronic board with microprocessor, which are configured to control the operation or shut-down of the electric motor. The control means are supplied with electric current.

In addition, the apparatus 10 can also comprise other elements, such as pressure sensors and flow rate sensors, pneumatic control elements, solenoid valve, non-return valve, a viewing screen, a human-machine interface (HMI), etc.

The air inlet 12 of the casing is in fluidic communication with an air source, preferably the ambient atmosphere, while the oxygen inlet 21 is in fluidic communication with an oxygen source, such as a gas canister containing oxygen, or a wall socket for distribution of gaseous oxygen, supplied though a gas channel or a network of channels. The gas coming from this gas source can also be filtered in order to hold back any dust or other particles.

Figure 9:
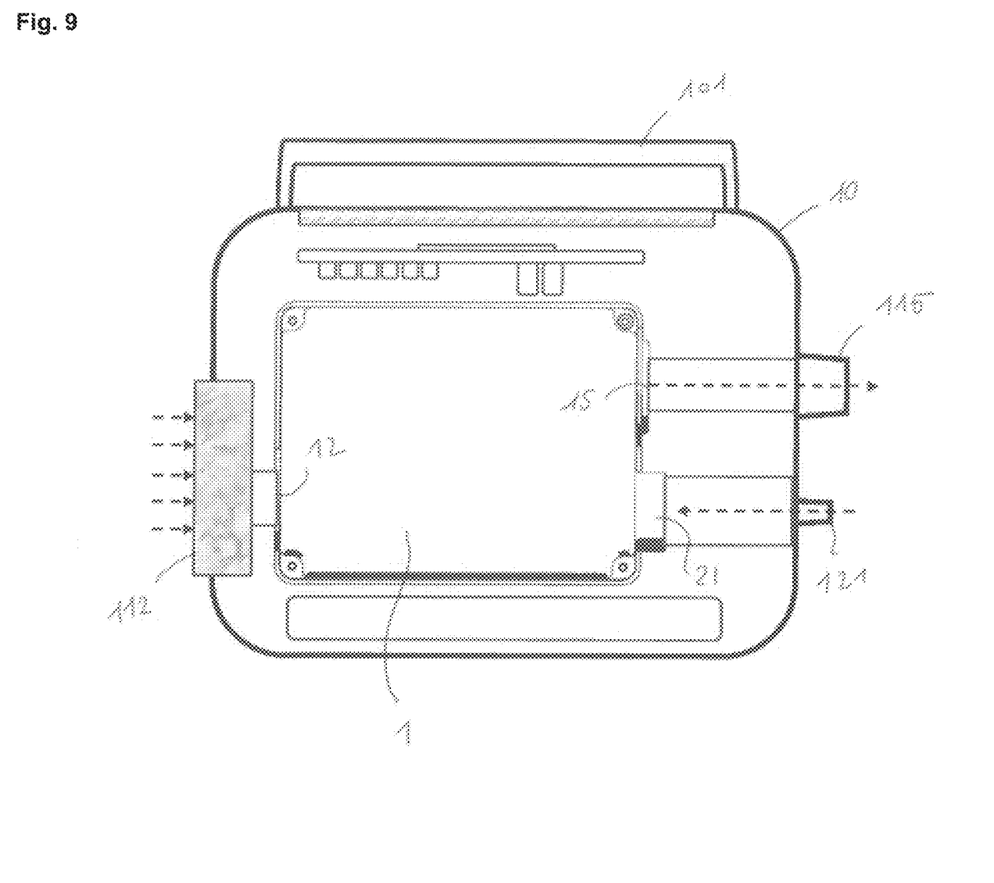
FIG. 9 shows an integration of the casing from FIG. 1 in a respiratory assistance apparatus.

FIG. 9 shows an integration of the casing 1 from FIG. 1 in a respiratory assistance apparatus or medical ventilator 10, typically an apparatus delivering gas at one or more pressure levels, that is to say a ventilator of the CPAP or BiPAP type.

As will be seen, the medical ventilator 10 comprises one or more air inlets 112 in fluidic communication with the one or more air inlet orifices 12 of the casing 1, and also an oxygen inlet 21 in fluidic communication with the one or more oxygen inlet orifices 21 of the casing. The medical ventilator 10 moreover comprises a gas flow outlet 115 in fluidic communication with the gas outlet passage 15 of the micro-blower, making it possible to evacuate the air/oxygen mixture in order then to convey it to a patient, via the gas distribution outlet 115 of the apparatus 10.

The one or more air inlets 112 are formed in the peripheral shell 102 of the apparatus 10, while the oxygen inlet 121 is arranged in an oxygen supply connector supported by the shell of the apparatus 10, connected fluidically to an oxygen source, such as a gas canister containing oxygen, or a wall socket for distribution of gaseous oxygen, supplied though a gas channel or a network of channels.

Moreover, the peripheral shell of the apparatus 10 can comprise a carrying handle 101 making it easier for a user to transport, as can be seen in FIG. 9.

In addition, the apparatus 10 can also comprise other elements (not shown), such as pressure sensors and flow rate sensors, pneumatic control elements, a viewing screen, a human-machine interface (HMI), etc.

Generally, a respiratory assistance apparatus 10 equipped with a casing according to the invention, integrating a micro-blower, is intended to treat respiratory diseases in human patients, i.e. adults and/or children.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A respiratory assistance apparatus (10) comprising a rigid casing (1) comprising a motor compartment (3) within which a motorized micro-blower (2) is arranged, characterized in that the casing (1) is formed from a first and a second half-casing (1a, 1b) which are rigidly connected to each other in a leaktight manner, said rigid casing (1) comprising:
    an air inlet compartment (11) comprising an air inlet opening (12) in communication with the atmosphere, said air inlet compartment (11) additionally being in fluidic communication with the motor compartment (3) via at least one air outlet opening (13),
    a gas outlet compartment (14) comprising a gas supply opening (15), said gas outlet compartment (14) being fed with gas by the motorized micro-blower (2),
    an oxygen circuit (16) comprising an oxygen inlet (17) and at least one oxygen outlet (18), said at least one oxygen outlet being in fluidic communication with the motor compartment (3), and
    a venting circuit (19) comprising an air inlet (20), formed in the air inlet compartment (11), and an air outlet (21).

2. The apparatus according to claim 1, characterized in that the first half-casing (1a) comprises:
    at least part of the air inlet compartment (11),
    at least part of the motor compartment (3),
    at least part of the gas outlet compartment (14), and
    the oxygen circuit (16) comprising the oxygen inlet (17) and said at least one oxygen outlet (18).

3. The apparatus according to claim 2, characterized in that the second half-casing (1b) comprises:
    at least part of the air inlet compartment (11), and
    the venting circuit (19) comprising the air inlet (20) and the air outlet (21).

4. The apparatus according to claim 3, characterized in that the venting circuit (19) comprises an air outlet (21) arranged parallel to the gas supply opening (15) of the gas outlet compartment (14).

5. The apparatus according to claim 3, characterized in that the oxygen circuit (16) comprises an oxygen inlet (17) arranged parallel to the air outlet (21) of the venting circuit (19).

6. The apparatus according claim 1, characterized in that the motor compartment (3) comprises a peripheral wall (3a) surrounding at least part of the outer housing (2a) of the micro-blower (2), thus defining, with said outer housing (2a), a space (22) for passage of gas.

7. The apparatus according to claim 6, characterized in that the oxygen circuit (16) comprises an oxygen outlet (18) opening into the gas passage space (22) situated between the peripheral wall (3a) of the motor compartment (3) and the outer housing (2a) of the micro-blower (2), so as to feed said space (22) of the motor compartment (12) with oxygen and to mix said oxygen there with the air coming from the air inlet compartment (11).

8. The apparatus according to claim 7, characterized in that the motorized micro-blower (2) additionally comprises a volute (23) defining a wheel compartment (27) which accommodates a bladed wheel (24) supported by a motor shaft (25) driven by the motor contained in the housing (2a) of the motorized micro-blower (2), said volute (23) comprising a volute opening (26) in fluidic communication with, on the one hand, the gas passage space (22) and, on the other hand, the wheel compartment (27).

9. The apparatus according to claim 8, characterized in that the volute (23) additionally comprises an outlet opening (28) in fluidic communication with, one the one hand, the wheel compartment (27) and, on the other hand, the gas outlet compartment (14).

10. An installation for supplying respiratory gas to a patient, comprising a respiratory assistance apparatus according to claim 1, an oxygen source, such as a pressurized oxygen canister, connected fluidically to said respiratory assistance apparatus, a flexible conduit connected fluidically to said respiratory assistance apparatus and fed with gas by said respiratory assistance apparatus, and a respiratory interface fed with gas by said flexible conduit.

* * * * *